United States Patent [19]
Okazaki

[11] Patent Number: 5,048,527
[45] Date of Patent: Sep. 17, 1991

[54] SHOCK WAVE TREATMENT APPARATUS

[75] Inventor: Kiyoshi Okazaki, Takanezawa, Japan

[73] Assignee: Kabushiki Kaisha Toshiba, Kawasaki, Japan

[21] Appl. No.: 271,876

[22] Filed: Nov. 16, 1988

[30] Foreign Application Priority Data

Nov. 16, 1987 [JP] Japan .............................. 62-290158
Jan. 13, 1988 [JP] Japan .................................. 63-3829

[51] Int. Cl.$^5$ .............................................. A61B 17/22
[52] U.S. Cl. ............................ 128/660.03; 128/24 EL
[58] Field of Search ............. 606/127, 128; 128/24 A, 128/660.03, 24 AA, 24 EL; 604/22

[56] References Cited

U.S. PATENT DOCUMENTS

| | | |
|---|---|---|
| 4,617,931 | 10/1986 | Dory . |
| 4,669,472 | 6/1987 | Eisenmenger ................... 128/24 A |
| 4,776,342 | 10/1988 | Zimmer ......................... 128/660.03 |
| 4,821,729 | 4/1989 | Makofski et al. ................. 128/24 A |
| 4,834,106 | 5/1989 | Hassler et al. ................... 128/24 A |
| 4,844,079 | 7/1989 | Naser et al. ................... 128/660.03 |
| 4,844,081 | 7/1989 | Northeved et al. ............. 128/660.03 |
| 4,928,672 | 5/1990 | Grasser et al. ................... 128/24 A |

FOREIGN PATENT DOCUMENTS

| | | |
|---|---|---|
| 0133946 | 6/1987 | European Pat. Off. . |
| 3736733 | 5/1988 | Fed. Rep. of Germany . |
| 62-49843 | 3/1987 | Japan . |

Primary Examiner—Ruth S. Smith
Attorney, Agent, or Firm—Oblon, Spivak, McClelland, Maier & Neustadt

[57] ABSTRACT

A shock wave treatment apparatus has a piezo-electric transducer for creating a convergent point of shock wave to crush a to-be-crushed object in a living body. A water tank filled with water is disposed under the shock wave transmission surface of the piezo-electric transducer. Further, an ultrasonic wave transducer is disposed in the water tank in the shock wave transmission range of the piezo-electric transducer and has an ultrasonic wave transmission/reception surface held in substantially the same plane as the bottom surface of the water tank. The ultrasonic wave transducer is used to collect tomographic image data of the living body with the ultrasonic wave transmission/reception surface set in contact with the surface of the living body.

10 Claims, 8 Drawing Sheets

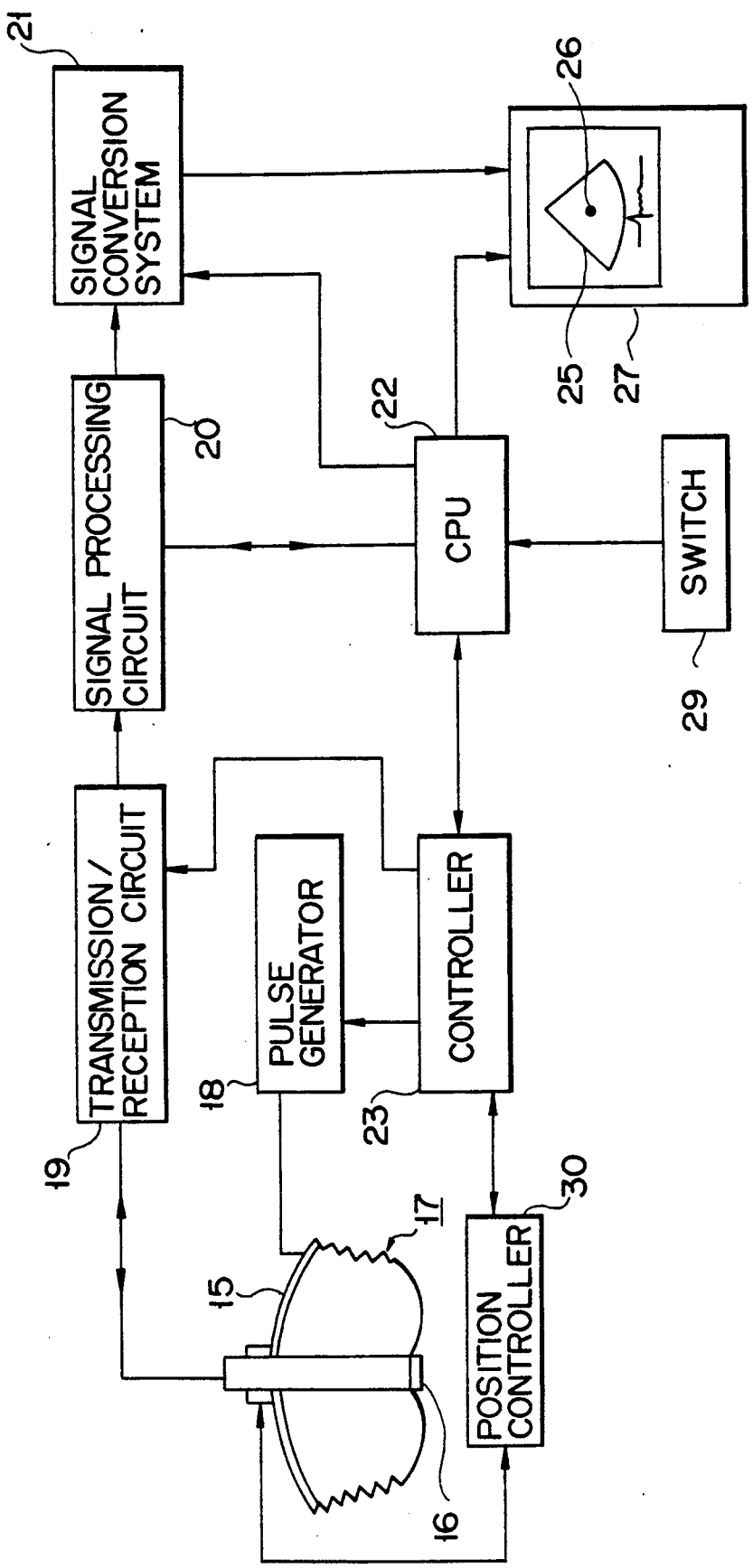
F I G. 3

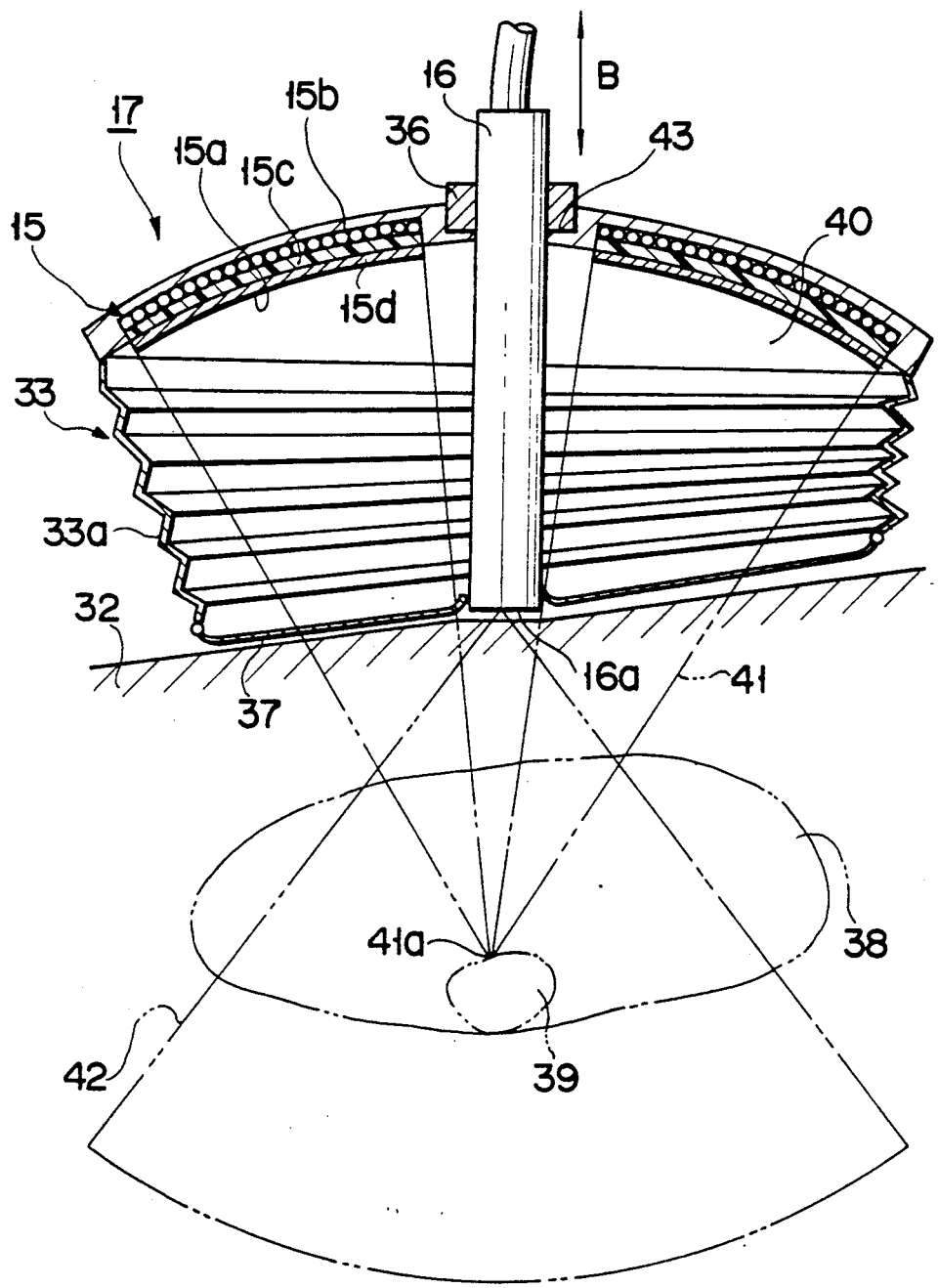
F I G. 9

SHOCK WAVE TREATMENT APPARATUS

BACKGROUND OF THE INVENTION

1. Field of the Invention

This invention relates to a shock wave treatment apparatus for treating a living body by crushing a gallstone, urinary calculus or the like in the living body with the concentrated energy of shock waves.

2. Description of the Related Art

One type of ultrasonic treatment apparatus is disclosed in Japanese Patent Disclosure (KOKAI) 62-049843. FIG. 1 is a cross section showing an ultrasonic applicator constituting the above ultrasonic treatment apparatus.

As shown in FIG. 1, ultrasonic applicator 1 includes concave transducer 2 having a radius of curvature of 5 cm and having a through hole formed with a predetermined shape in its center, and backing member 3 uniformly formed on the back side of concave transducer 2.

Ultrasonic transducer 4 is a sector probe which is fixed in the through hole and has transducer array 4a of narrow transducer elements arranged in alignment with the concave surface of concave transducer 2.

In FIG. 1, 5 denotes an acoustic coupler constituted by bag 6 which is filled with water and is formed of a thin film having an acoustic impedance substantially equal to that of water.

Further, an ultrasonic treatment apparatus disclosed in article "Die Zertrümmerung von Nierensteinen mit einem piezoelektrischen Gerätesystem" by M. Ziegler et al, Urologe [A] (1986) 25:193-197 and including ultrasonic applicator 7 shown in FIG. 2 is also used.

Applicator 7 shown in FIG. 2 includes concave transducer 9 which corresponds to concave transducer 2 shown in FIG. 1 and is disposed below bed 8, water tank 10 filled with water and defined by the ultrasonic wave transmission/reception surface of concave transducer 9 and opening 13 formed in bed 8, and ultrasonic applicator 11 disposed inside water tank 10.

In FIG. 2, 12 shows the manner in which the shock wave transmitted from concave transducer 9 is converged.

In general, the above conventional ultrasonic treatment apparatus are understood to have the following defects:

In the ultrasonic treatment apparatus disclosed in Japanese Patent Disclosure (KOKAI) 62-049843, the front end surface of ultrasonic array 4a acting as the ultrasonic wave transmission/reception surface of ultrasonic wave transducer 4 of ultrasonic applicator 1 is arranged in the same curved plane as the ultrasonic wave transmission/reception surface of concave transducer 2 or behind the curved plane.

The quality of the displayed image of a to-be-crushed object is generally dependent on the width of the transmission/reception surface and the distance from the transmission/reception surface to the convergent point. With the above construction, the distance from the transmission/reception surface of ultrasonic wave transducer 4 to the stone is made long because of the presence of water in acoustic coupler 5 and the thin film constituting acoustic coupler 5. Therefore, it is impossible to prevent the ultrasonic wave from being scattered and attenuated, and the displayed image on the display unit will be influenced by noise, making it difficult to correctly recognize the to-be-crushed object.

In contrast, the ultrasonic treatment apparatus disclosed in the article "Urologe [A] (1986) 25:193-197" has the defects caused by use of the mechanical probe. For example, the quality of the displayed image is lowered, the whole size becomes large, it is mechanically weak and easily affected by vibration, and it is difficult to operate the ultrasonic applicator since it is fixedly mounted on the bed.

SUMMARY OF THE INVENTION

An object of this invention is to provide a shock wave treatment apparatus with which the above problems can be effectively solved, the quality of displayed image is enhanced to attain a distinct picture image, and the to-be-crushed object can be easily and precisely recognized.

In order to achieve the above object, a shock wave treatment apparatus of this invention comprises shock wave transducer means for creating a converging point of the shock wave for crushing a to-be-crushed object existing in a living body; pulser means for supplying a pulse signal to said shock wave transducer means; a water tank mounted to provide water under the shock wave transmission surface of the shock wave transducer means; image information collecting means arranged in a shock wave transmission range of the shock wave transducer means and having an ultrasonic wave transmission/reception surface held in substantially the same plane as the bottom surface of the water tank, and for collecting tomographic image data of the living body with the ultrasonic wave transmission/reception surface set in contact with the surface of the living body; and image information processing means connected to said image information collecting means and for processing the collected image information.

In the shock wave treatment apparatus of this invention with the above construction, since the distance from the ultrasonic wave transmission/reception surface of the shock wave transducer means to the convergent point inside the living body can be made shorter, the scattering and attenuation of the ultrasonic wave can be suppressed and influence due to noise can also be suppressed, making it possible to enhance the quality of the picture image.

BRIEF DESCRIPTION OF THE DRAWINGS

FIG. 3 is a block diagram showing the circuit construction of a shock wave treatment apparatus according to one embodiment of this invention;

FIG. 9 is a cross sectional view of a shock wave applicator of a shock wave treatment apparatus according to another embodiment of this invention;

DETAILED DESCRIPTION OF THE PREFERRED EMBODIMENTS

Figure 1:
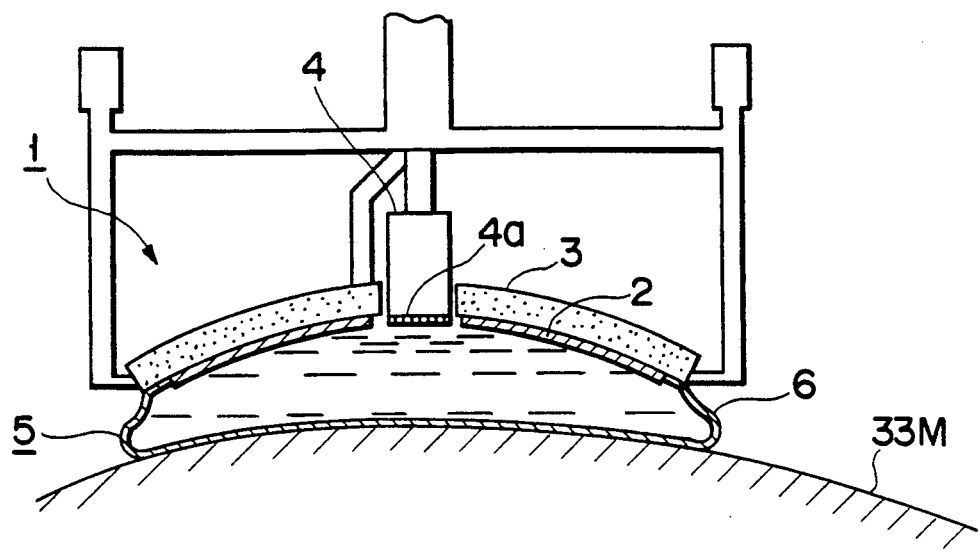
FIG. 1 is a cross sectional view of a shock wave applicator of the conventional shock wave treatment apparatus.
Figure 2:
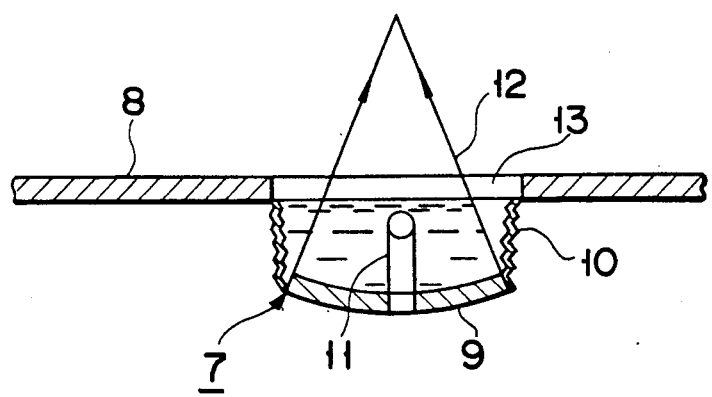
FIG. 2 is a cross sectional view of a shock wave applicator of the conventional shock wave treatment apparatus mounted on the bed.

There will now be explained an embodiment of this invention in which a piezo-electric transducer is used as the shock wave transducer means with reference to FIGS. 3 to 7. FIG. 3 is a block diagram showing the construction of the shock wave treatment apparatus of this invention. As shown in FIG. 3, the shock wave treatment apparatus includes piezo-electric transducer 15 for transmitting a shock wave which is created by an ultrasonic wave as will be described later; shock wave applicator 17 constituted to include ultrasonic wave transducer 16 for transmitting or receiving the ultrasonic wave establishing an acoustic area which is different from the shock wave transmission/reception range set up by piezo-electric transducer 15; pulser 18 for supplying a pulse signal to piezo-electric transducer 15; transmission/reception circuit 19 for supplying a pulse signal to excite ultrasonic wave transducer 16 so as to effect the sector scanning operation and receiving an echo signal supplied from ultrasonic wave transducer 16 as a result of the scanning operation; and signal processing circuit 20 for subjecting an output signal of transmission/reception circuit 19 to amplitude-detection and supplying the resultant signal as a video signal to signal conversion system 21. It further includes central processing unit (CPU) 22 for controlling various parts of the treatment apparatus using preset parameters; controller 23 for controlling the transmission/reception timings, amplitude, frequency and the like of the pulse signal in transmission/ reception circuit 19, signal processing circuit 20 and pulse generator 18 under the control of CPU 22; signal conversion system (for example, digital scanning converter) 21 for subjecting output signals of transmission/ reception circuit 19 and signal processing circuit 20 to the signal conversion process under the control of CPU 22; display unit 27 including TV monitor or the like for displaying the body surface image of the living body, kidney image, kidney stone image, sector acoustic area 25 and the like established by ultrasonic wave transducer 16 based on the output signal of signal conversion system, and the shock wave transmission area of piezo-electric transducer 15, convergent point marker 26 and the like; pulse generation switch 29 having first and second switches (not shown) and connected to CPU 22 to set the generation timing of the pulse signal supplied from pulse generator 18 to piezo-electric transducer 15; and position controller 30 for adjusting the relative position of ultrasonic wave transducer 16 with respect to piezo-electric transducer 15.

Now, shock wave applicator 17 will be described more in detail with reference to FIGS. 4 to 7.

Figure 4:
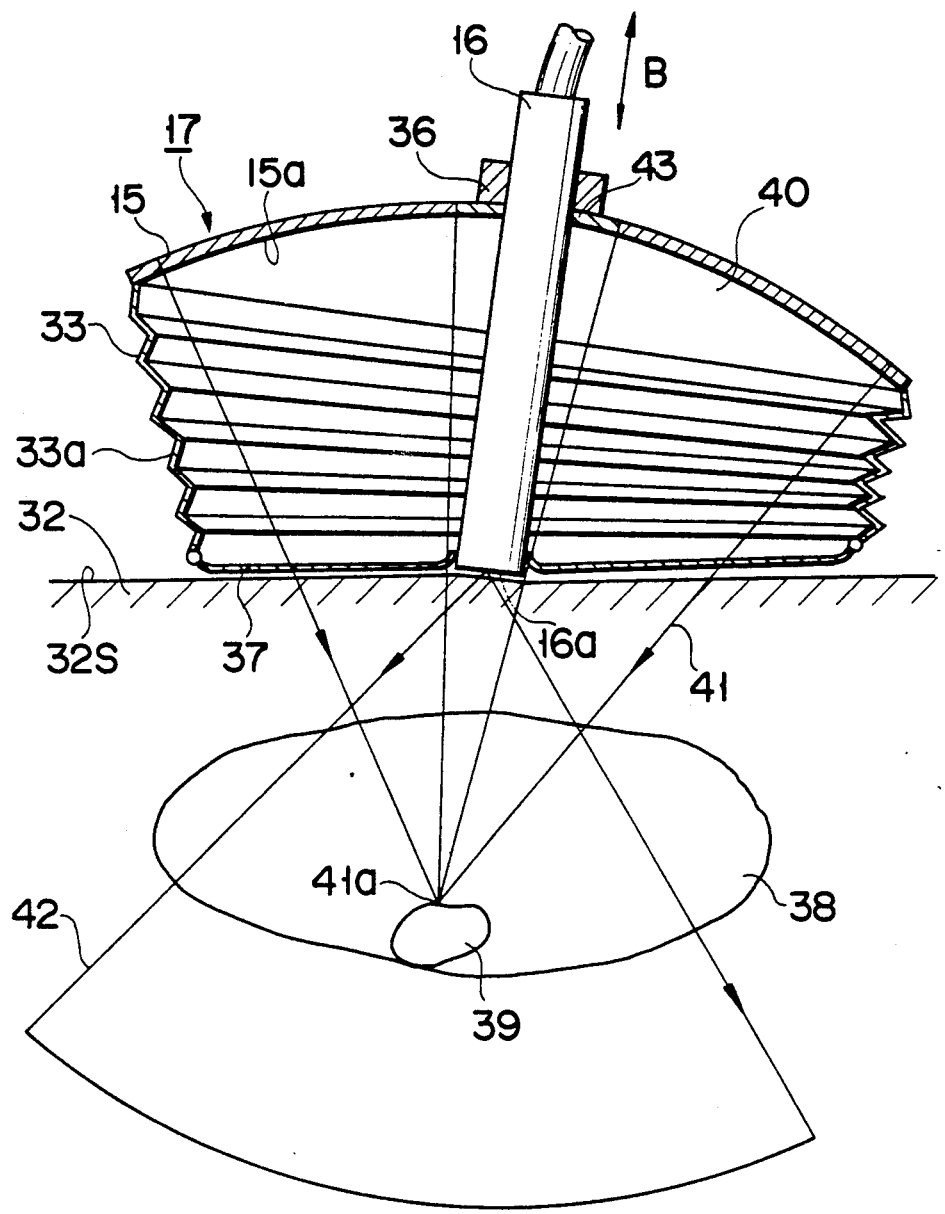
FIG. 4 is a cross sectional view of a shock wave applicator of a shock wave treatment apparatus according to one embodiment of this invention.

As shown in FIG. 4, shock wave applicator 17 includes piezo-electric transducer 15 for setting convergent point 41a of crushing shock wave (for example, ultrasonic wave pulse of strong energy) to crush a to-be-crushed object such as a kidney stone in living body 32, water tank 33 disposed on the side of shock wave transmission surface 15a of piezo-electric transducer 15, and ultrasonic transducer 16 arranged in shock wave transmission area 41 ranging from shock wave transmission surface 15a of piezo-electric transducer 15 to convergent point 41a and used for forming acoustic area 42 including convergent point 41a with ultrasonic wave transmission/reception surface 16a set in contact with living body surface 32S so as to collect tomographic image data of living body 32.

Piezo-electric transducer 15 is constituted to include a concave transducer with predetermined curvature. In the central portion of piezo-electric transducer 15, ultrasonic wave transducer 16 is mounted via transducer supporting/driving section 36 so as to be movable in a direction indicated by arrow B.

The range of the waves which are driven by piezo-electric transducer 15 can be widened if the convergence point of shock waves is located away from living body surface 32S, or is narrowed if the converging point is close to living body surface 32S. In the case where the converging point is located close to living body surface 32S, some of the shock waves emitted from piezo-electric transducer 15 may collide against the outer wall of ultrasonic transducer 16 and may not reach the convergence point. Even these shock waves can reach the covergence point by adjusting the position of ultrasonic transducer 16 so that the transducer is moved more away from living body surface 32S. In the present invention, therefore, all shock waves can be made to reach the convergence point.

Transducer supporting/driving section 36 includes a mechanism which can be freely moved and stopped in the direction indicated by arrow B and a driving source for driving the mechanism in response to a control signal from position controller 30. In this embodiment, a rack member is fixed on the surface of ultrasonic wave transducer 16, and a motor is provided with a driving shaft on which a pinion gear engaged with the rack is mounted. With this construction, the rotation amount or rotation angle of the motor is controlled by means of position controller 30 so as to adjust the relative position between piezo-electric transducer 15 and ultrasonic wave transducer 16. In this case, transducer supporting/driving section 36 can be designed to have a different construction, and it is not an indispensable component. That is, ultrasonic transducer 16 may be fixed on the central portion of piezo-electric transducer 15, or it can be mounted so as to be manually moved in the direction of arrow B when a constant force is applied thereto in the direction of arrow B.

In this embodiment, water tank 33 filled with water used as a shock wave transmission medium is disposed below shock wave transmission surface 15a of piezo-electric transducer 15.

Water tank 33 shown in FIG. 4 is formed to have a hollow bottomed cylinder or hollow, truncated cone whose diameter is substantially equal to the outer diameter of piezo-electric transducer 15. Water tank 33 has bellows 33a which is mounted on the side surface thereof and is capable of expansion and contraction in the direction of arrow B or a direction within a preset angle with respect to the direction. Further, bottom portion 37 of water tank 33 is formed of a thin film having substantially the same acoustic impedance as water. The detail construction thereof is shown in FIG. 6.

Figure 5:
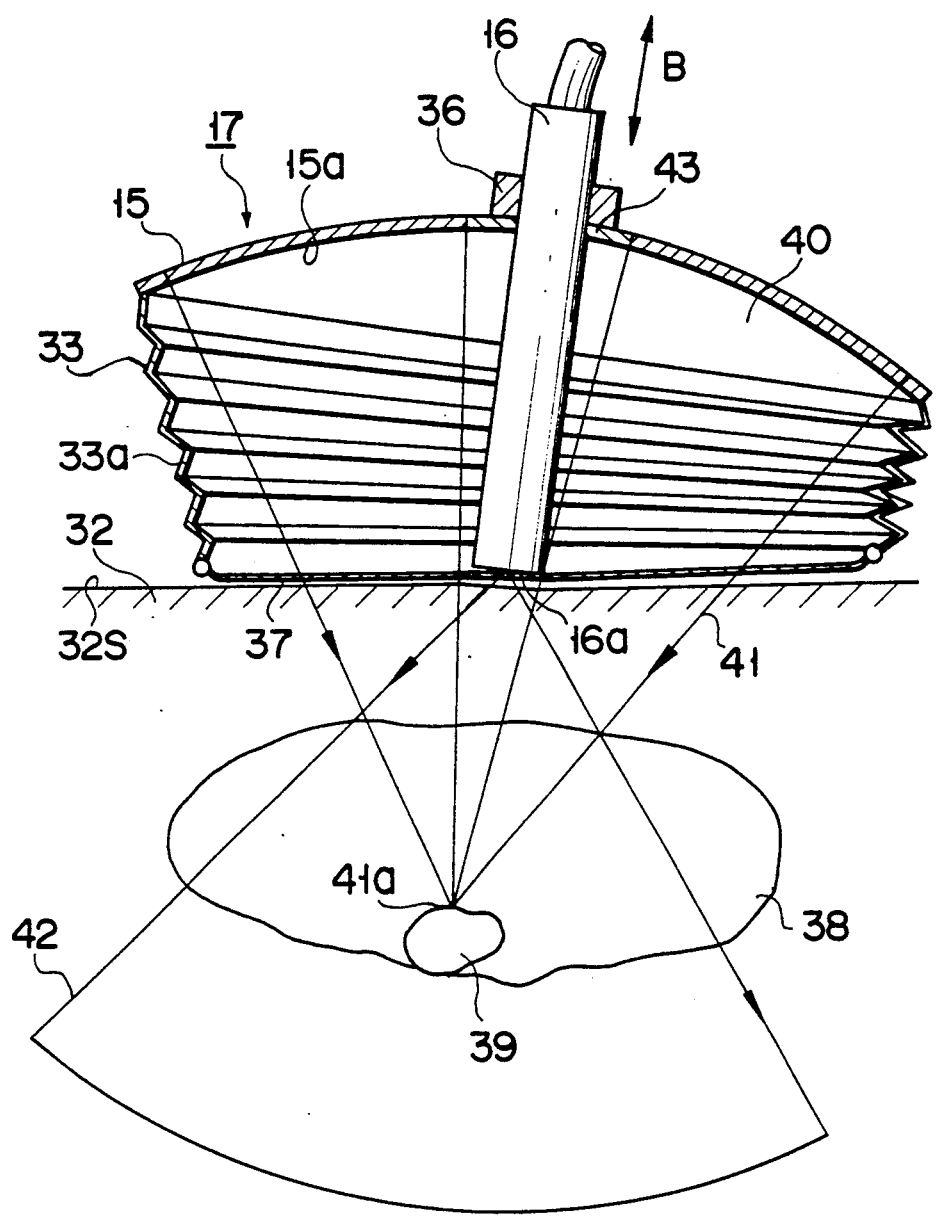
FIG. 5 is a cross sectional view showing a modification of the FIG. 4 embodiment in which the ultrasonic wave transmission/reception surface of an ultrasonic wave transducer abuts against the surface of the living body via a thin film.
Figure 6:
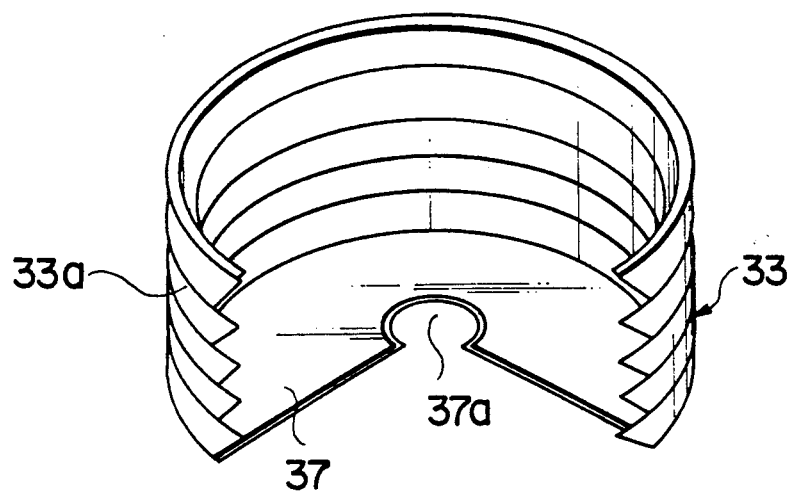
FIG. 6 is a view showing a water tank of FIG. 4 partly in cross section.

As shown in FIG. 6, cut-away portion 37a corresponding in shape to the side surface of ultrasonic wave transmission/reception surface 16a of ultrasonic wave transducer 16 is formed in the central portion of bottom portion 37 of water tank 33. In this embodiment, the peripheral surface of cut-away portion 37a is fixedly welded or bonded to the side surface of ultrasonic wave transducer 16 near ultrasonic wave transmission/ reception surface 16a. Thus, the thin film can be deformed according to the movement of ultrasonic wave transducer 16 so that ultrasonic wave transmission/ reception surface 16a can be freely moved in contact with living body surface 32S. Further, as shown in FIG. 5, the construction can be so modified as to set ultrasonic wave transmission/reception surface 16a in contact with living body surface 32S via the thin film. In FIG. 5, parts which correspond to those in FIG. 4 are denoted by the same reference numerals and the explanation therefor is omitted. In this case, bellows 33a is constituted to hold its shape when an external force is not applied thereto. This can be attained by properly selecting the material of bellows 33a or using an auxiliary member, for example.

Figure 7:
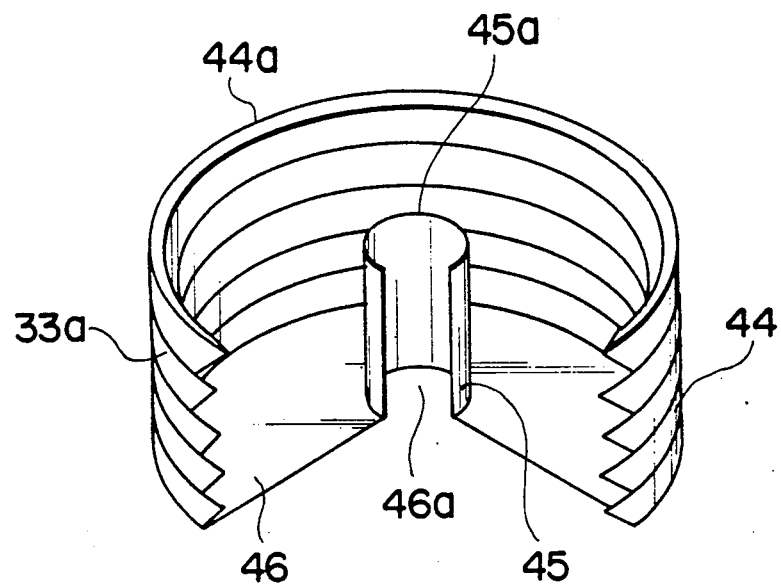
FIG. 7 is a partially cross sectional view showing another construction of the water tank of FIG. 4.

FIG. 7 shows another example of water tank 33.

Figure 8:
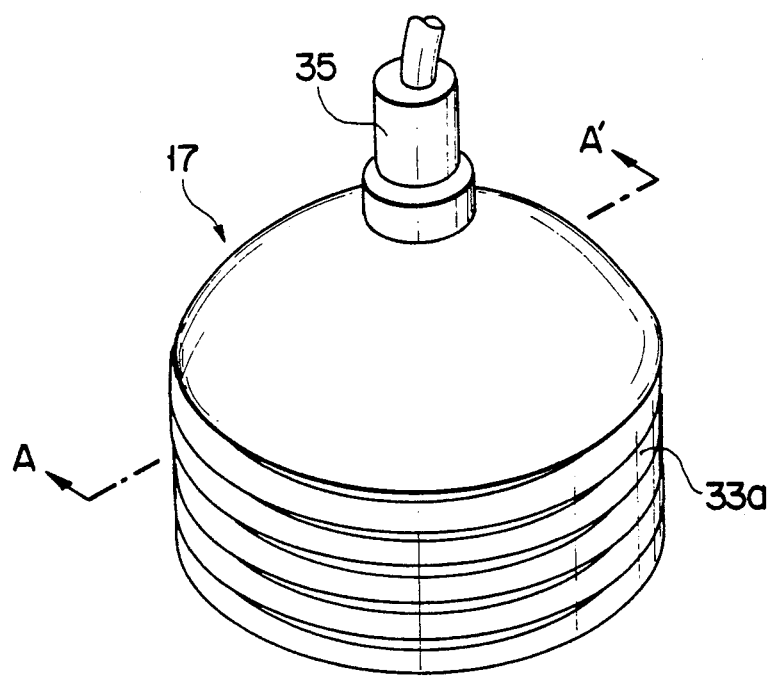
FIG. 8 is a perspective view of the shock wave applicator shown in FIG. 4.

Water tank 44 shown in FIG. 7 is the same as that of FIG. 6 in that bellows 33a is formed on the side surface. However, it is different in that cylindrical member 45 having the same shape as cut-away portion 46a which is formed in the central portion of bottom portion 46 is formed. That is, cylindrical member 45 having substantially the same diameter as that of cutaway portion 46a is formed to have substantially the same height as that from bottom portion 46 to the upper end of the side surface. Upper end 45a of cylindrical member 45 is bonded to the periphery of cut-away portion 43 formed in the central portion of piezo-electric transducer 15 shown in FIGS. 4 and 5. Therefore, when water tank 44 is mounted on piezo-electric transducer 15, water filling water tank 44 will not leak out. With this construction ultrasonic transducer 16 is inserted into cylindrical member 45. In this case, cylindrical member 45 may be formed integrally with the bottom portion of water tank 44 or may be formed with different material. The appearance of the shock wave applicator with the above construction is shown in FIG. 8. In the water tank shown in FIGS. 6 and 7, the bellows is formed on the side surface thereof, but is can be omitted and may be selectively formed as required.

Assuming the case wherein kidney stone 39 existing in kidney denoted by 38 in FIG. 4 is crushed or treated, the operation and effect of the shock wave treatment apparatus of the above construction is explained.

First, water tank 33 formed in shock wave applicator 17 is placed on surface 32S of living body 32. Under this condition, transmission/reception circuit 19, signal processing circuit 20 and signal conversion system 21 are controlled to drive ultrasonic wave transducer 16, and the tomographic image of the living body is displayed on the screen of display unit 27. In this case, since transmission/reception surface 16a of ultrasonic wave transducer 16 is set in direct contact with living body surface 32S, the clear tomographic image can be obtained without being affected by the bottom portion of water tank 33, water and the like. In this way, the to-be-crushed object can be easily detected and recognized.

When kidney image 38 is obtained in the tomographic image, kidney stone image 39 included therein is detected.

In this case, the position of the concave transducer (not shown), shock wave transmission area 41 and convergent point marker 26 of piezo-electric transducer 15 are respectively displayed on the fixed portions of display unit 27 according to signals transferred between CPU 22 and signal conversion system 21. The display position of the tomographic image of living body 32 displayed on the real time basis is changed according to the movement of shock wave applicator 17. At this time, since transmission/reception surface 16a of ultrasonic wave transducer 16 is arranged in the shock wave transmission area ranging from transmission surface 15a of piezo-electric transducer 15, it is possible to set the display position of the to-be-crushed object in the central portion of the display screen. As a result, the to-be-crushed object can be easily recognized. Further, since the relative position between ultrasonic wave transducer 16 and shock wave transducer 15 can be adjusted, the treatment or therapy operation can be further simplified.

When kidney stone image 39 is obtained in the tomographic image, the position of shock wave applicator 17 is precisely adjusted so as to set kidney stone image 39 in convergent point marker 26, and in this condition, shock wave applicator 17 is fixed. In this case, since bellows 33a holds the previously set shape thereof, the shock wave applicator can be easily fixed.

Next, the operator operates a first switch (not shown) of pulse generation switch 29 shown in FIG. 3 to supply a control signal to pulse generator 18 via CPU 22 and controller 23. As a result, a pulse signal is transmitted from pulse generator 18 to piezo-electric transducer 15, causing piezo-electric transducer 15 to transmit an ultrasonic pulse of strong energy (shock wave for crushing the to-be-crushed object) towards kidney stone 39 existing in position corresponding to the position of convergent point marker 26.

The ultrasonic wave pulse is converted into a shock wave in the convergent point to crush the kidney stone.

Kidney stone 39 can be entirely crushed by repeatedly generating the ultrasonic pulse by a required number of times.

This invention is not limited to the embodiments described above and can be variously modified within the technical scope thereof.

For example, in the above embodiments, the case wherein the kidney stone is crushed is explained, but it is possible to crush a gallstone. Further, in the case where water tank 33 or 44 shown in FIG. 6 or 7 is used, the effect that the waterproof process for the ultrasonic transmission/reception surface of the ultrasonic wave transducer is not required is obtained in addition to the aforementioned effect.

Now, a treatment apparatus having a shock wave applicator which is provided with an electromagnetic induction type sound source used as the shock wave generation means is explained as another embodiment of this invention with reference to FIGS. 9 to 12.

Figure 10:
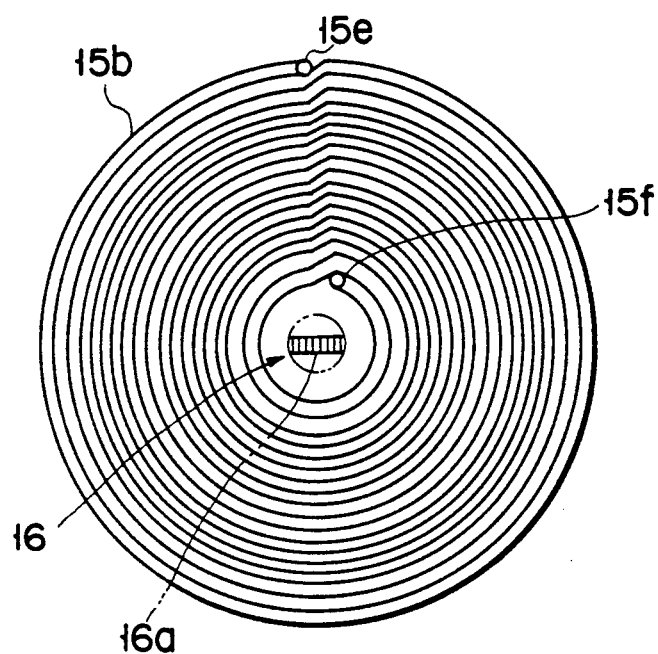
FIG. 10 is a plan view showing a coil portion of shock wave transducer means constituting the shock wave applicator of FIG. 9.

As shown in FIGS. 9 and 10, shock wave generation means 15 in this embodiment includes coil 15b formed in a circular concave form having a preset curvature and wound in a spiral form with image information collecting means 16 used as a center, and metal film 15d disposed on coil 15b via insulation member 15c. Shock wave transmission surface (vibration plane) 15a of shock wave generation means 15 is formed in the concave form, causing the sound wave generated towards living body 32 to be converged in living body 32 and converted into a shock wave.

Figure 11:
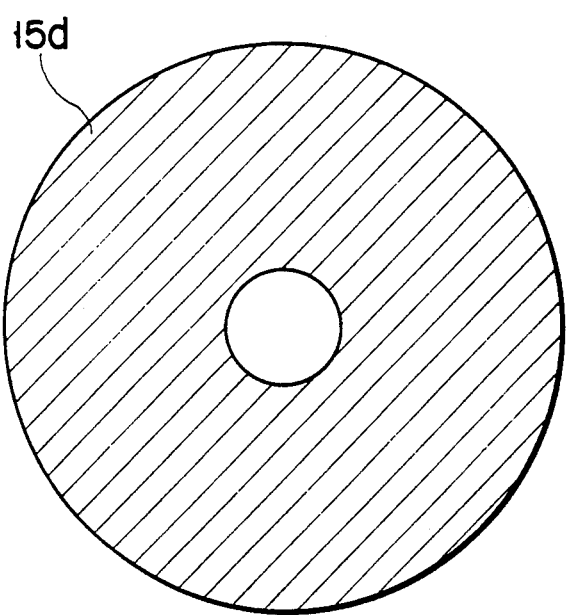
FIG. 11 is a plan view of a metal film of the shock wave transducer means constituting the shock wave applicator of FIG. 9.

FIGS. 10 and 11 are plan view showing coil 15b and metal film 15d, respectively. Two ends 15e and 15f of spirally wounded coil 15b are electrically connected to output ends of pulser 18, and a shock wave generation signal is supplied from pulser 18 to coil 15b. In this case, when the shock wave generation signal is supplied to coil 15b, a reverse current flows in metal film 15d by the electromagnetic induction effect, and metal film 15d is abruptly pushed off by a magnetic force occurring in opposite directions between coil 15b and metal film 15d, thus generating a sound wave. In other word, a so-called electromagnetic induction type sound source including coil 15b, insulation member 15c and metal film 15d is provided. In this embodiment, shock wave generation means 15 is constituted to include the single electromagnetic induction type sound source.

Image information collecting means 16 is provided in the center of shock wave generation means 15. As image information collecting means 16, an ultrasonic probe which has a plurality of ultrasonic wave transducers and obtain image information (B mode information) of an area in living body 32 by sector-scanning the ultrasonic wave is used.

Figure 12:
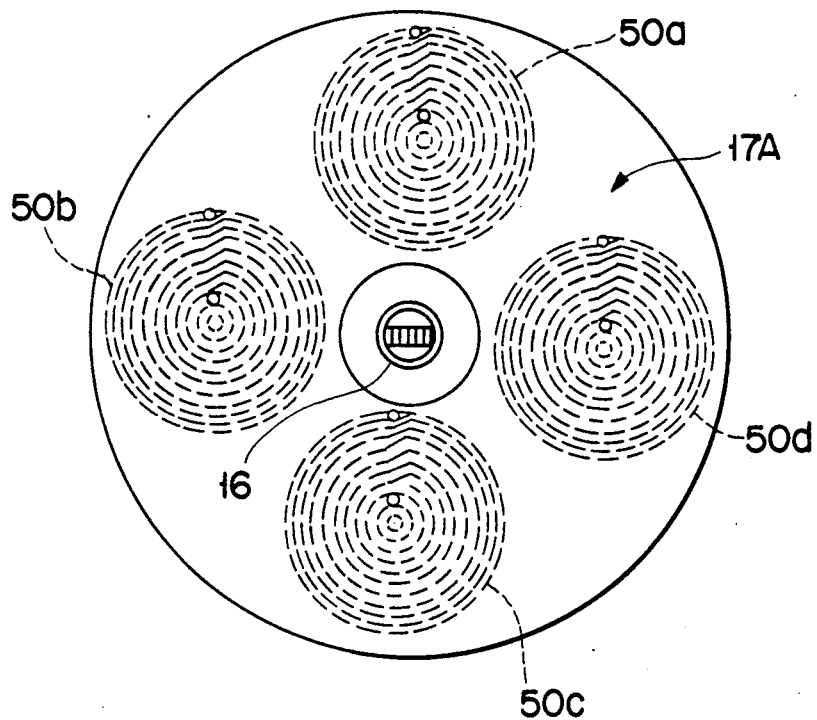
FIG. 12 is a plane view of a shock wave applicator showing an embodiment in which a plurality of electromagnetic induction type sound sources are arranged.

In the above embodiment, shock wave generation means 17 is formed of a single electromagnetic induction type sound source, but it is possible to use a plurality of electromagnetic induction type sound sources. In FIG. 12, 17 denotes a shock wave applicator 17A includes four electromagnetic induction type sound sources 50a, 50b, 50c and 50d with image information collecting means 16 positioned at the center of the arrangement. Each of electromagnetic induction type sound sources 50a, 50b, 50c and 50d includes a coil spirally wounded in the same manner as in the former embodiment, and a metal film disposed on the coil via an insulation member. The sound wave generated from each sound source is converged in the living body and converted into a shock wave.

As described above, in this embodiment, since the electromagnetic induction type sound source or sources are provided, a strong crushing shock wave can be transmitted. Further, the position of a to-be-crushed object can be detected based on the image information obtained by transmitting and receiving the ultrasonic wave, and unlike the prior art, an X-ray image obtained by application of X-ray is not used to detect the position of the to-be-crushed object. Therefore, the living body is not exposed to the X-ray and the whole size of the apparatus can be easily made small.

This invention is not limited to the embodiments described above and can be variously modified within the technical scope thereof.

What is claimed is:

1. A shock wave treatment apparatus comprising:
    shock wave generation means for creating a shock wave which converges to a converging point for crushing a to-be-crushed object in a living body said shock wave generation means having a shock wave transmission surface;
    pulser means for supplying a pulse signal to said shock wave generation means;
    a water tank mounted below the shock wave transmission surface of said shock wave generation means and containing water, said water tank having a bottom surface;
    image information collecting means arranged between said transmission surface and said converging point of the shock wave generation means and having an ultrasonic wave transmission/reception surface held in substantially the same plane as the bottom surface of said water tank, and for collecting tomographic image data of the living body with the ultrasonic wave transmission/reception surface adapted to be set in contact with the surface of the living body; and
    image information processing means connected to said image information collecting means for processing the collected image information;
    means for displaying said processed image information;
    wherein said water tank includes a substantially cylindrical body having a through hole for permitting said image information collecting means to be supported therein and moved in a direction substantially perpendicular to the bottom surface of said water tank.

2. A shock wave treatment apparatus according to claim 1, wherein said shock wave generation means comprises a piezoelectric transducer.

3. A shock wave treatment apparatus according to claim 1, wherein said shock wave generation means comprises an electromagnetic induction type sound source.

4. A shock wave treatment apparatus according to claim 3, wherein said electromagnetic induction type sound source includes a coil spirally wound and formed in a circular shape having a predetermined curvature; a metal film and an insulation member interposed between said metal film and said coil.

5. A shock wave treatment apparatus according to claim 1, wherein said shock wave generation means comprises a plurality of electromagnetic induction type sound sources arranged on a circle with said image information collecting means positioned at the center thereof.

6. A shock wave treatment apparatus comprising:
    shock wave generation means for creating a shock wave which converges to a converging point for crushing a to-be-crushed object in a living body, said shock wave generation means having a shock wave transmission surface;
    pulser means for supplying a pulse signal to said shock wave generation means;
    a water tank mounted below the shock wave transmission surface of said shock wave generation means and containing water, said water tank having a bottom surface;
    image information collecting means arranged between said transmission surface and said converging point of the shock wave generation means and having an ultrasonic wave transmission/reception surface held in substantially the same plane as the bottom surface of said water tank, and for collecting tomographic image data of the living body with the ultrasonic wave transmission/reception; and
    image information processing means connected to said image information collecting means for processing the collected image information;

means for displaying said processed image information;

wherein the bottom surface of said water tank is formed of a thin film, and said image information collecting means transmits and receives ultrasonic waves with respect to the to-be-crushed object in the living body through said thin film with the transmission/reception surface set in contact with the inner surface of said thin film.

7. A shock wave treatment apparatus according to claim 6, wherein said shock wave generation means comprises a piezoelectric transducer.

8. A shock wave treatment apparatus according to claim 6, wherein said shock wave generation means comprises an electromagnetic induction type sound source.

9. A shock wave treatment apparatus according to claim 8, wherein said electromagnetic induction type sound source includes a coil spirally wound and formed in a circular shape having a predetermined curvature; a metal film and an insulation member interposed between said metal film and said coil.

10. A shock wave treatment apparatus according to claim 6, wherein said shock wave generation means comprises a plurality of electromagnetic induction type sound sources arranged on a circle with said image information collecting means positioned at the center thereof.

* * * * *